(12) United States Patent
Sun et al.

(10) Patent No.: US 8,314,237 B2
(45) Date of Patent: Nov. 20, 2012

(54) PREPARATION OF 10-KETO MORPHINANS BY BENZYLIC OXIDATION

(75) Inventors: Hang Sun, Chesterfield, MO (US); John E. Johnson, Jr., Maryville, IL (US); Ricky L. Fenton, Maryville, IL (US); Sarah M. Dorn, Arnold, MO (US)

(73) Assignee: Mallinckrodt LLC, Hazelwood, MO (US)

( * ) Notice: Subject to any disclaimer, the term of this patent is extended or adjusted under 35 U.S.C. 154(b) by 206 days.

(21) Appl. No.: 12/876,284

(22) Filed: Sep. 7, 2010

(65) Prior Publication Data
US 2011/0071296 A1 Mar. 24, 2011

Related U.S. Application Data

(60) Provisional application No. 61/243,569, filed on Sep. 18, 2009.

(51) Int. Cl.
C07D 489/08 (2006.01)
C07D 489/02 (2006.01)
(52) U.S. Cl. .......................................... 546/45; 546/44
(58) Field of Classification Search .................. 546/45, 546/44
See application file for complete search history.

(56) References Cited

OTHER PUBLICATIONS

Sasaki Tadashi et al., "Studies on morphine-like compounds. IV. Oxidation of N-methylmorphinan and related compounds", Chemical and Pharmaceutical Bulletin, Pharmaceutical Society of Japan, Tokyo, vol. 15, No. 9, Sep. 25, 1967, pp. 1415-1419.
Archer et al., "10 Ketonaltrexone and 10 Ketooxymorphone", J. Med. Chem., 1985, 28, pp. 974-976.
Cain et al., "Sequentia Benzylic Oxidation of Naloxone 3-Methyl Ether", Synthetic Communications, 30(24), 2000, pp. 4513-4521.
Horikiri et al., "A Convenient Oxidation Method of the Benzylic 10-Position in 4,5-Epoxymorphinan", Heterocycles, 63(4), 2004, pp. 865-870.
Rapoport et al., "The Stereochemistry of 10-Hydroxycodeine Derivatives", Stereochemistry of 10-Hydroxycodeine, 77, 1955, pp. 4330-4335.
Salerno et al., "A Simple Synthesis of Photolabile α-Methyl Nitrobenzyl Compounds", Synthetic Communications, 34(13), 2004, pp. 2379-2386.
Uyeda et al., "10-Keto Opiates", Tetrahedron Letters, 30(42), 1989, pp. 5725-5728.
Yamazaki, "Chromium(VI) Oxide-Catalyzed Benzylic Oxidation with Periodic Acid", Organic Letters, 1(13), 1999, pp. 2129-2132.
Ceriliant's Website, http://www.cerliliant.com, downloaded Mar. 2009.

*Primary Examiner* — Charanjit Aulakh

(57) ABSTRACT

The present invention provides processes for the preparation of 10-keto and/or 10-hydroxy morphinans. In particular, the invention provides to processes for preparing a 10-keto morphinan by chromium-catalyzed benzylic oxidation of a morphinan with a periodic acid.

19 Claims, No Drawings

PREPARATION OF 10-KETO MORPHINANS BY BENZYLIC OXIDATION

CROSS REFERENCE TO RELATED APPLICATIONS

This application claims the benefit of U.S. Provisional Application No. 61/243,569 filed Sep. 18, 2009, which is incorporated herein in its entirety.

FIELD OF THE INVENTION

The present invention relates to the synthesis of 10-keto and/or 10-hydroxy morphinans. In particular, the invention relates to processes for preparing a 10-keto morphinan by chromium-catalyzed benzylic oxidation of a morphinan with a periodic acid.

BACKGROUND OF THE INVENTION

10-Keto and 10-hydroxy morphinans are common degradants of narcotic analgesics and opioid pharmaceutical products. Sufficiently pure 10-keto and/or 10-hydroxy morphinans are frequently needed for manufacturing and quality control processes, as well as for clinical and pharmaceutical studies. It is not practical to isolate these low-level impurities by preparative HPLC, however. Accordingly, synthetic methods are needed to provide sufficient amounts of pure materials for follow-up studies. Currently available methods for the synthesis of 10-keto and/or 10-hydroxy morphinans, however, have several disadvantages and limitations. For example, many methods have extremely low yields, are difficult to replicate, and/or require harsh reaction conditions, large amounts of metal oxidants, and/or protection of the basic nitrogen. There is a need, therefore, for new, convenient, and reliable methods for the synthesis of 10-keto and/or 10-hydroxy morphinans.

SUMMARY OF THE INVENTION

The present invention provides processes for the preparation of a 10-keto morphinan by benzylic oxidation of a morphinan. The benzylic oxidation process comprises chromium-catalyzed oxidation with periodic acid.

Briefly, therefore, one aspect of the present invention encompasses a process for the preparation of a 10-keto morphinan. The process comprises contacting a morphinan comprising hydrogen substituents on C-10 with an oxidizing system. The oxidizing system comprises a periodic acid and a chromium catalyst, wherein contact between the oxidizing system and the morphinan leads to the formation of the 10-keto morphinan.

Another aspect of the present invention provides a process for preparing a compound comprising Formula (II):

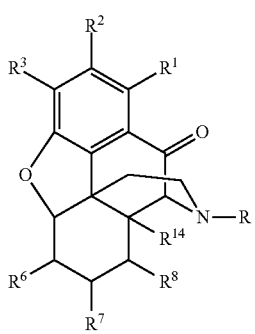

(II)

The process comprises contacting a compound comprising Formula (I) with an oxidizing system to form the compound comprising Formula (II). The oxidizing system comprises a periodic acid and a chromium catalyst. The compound of Formula (I) comprises:

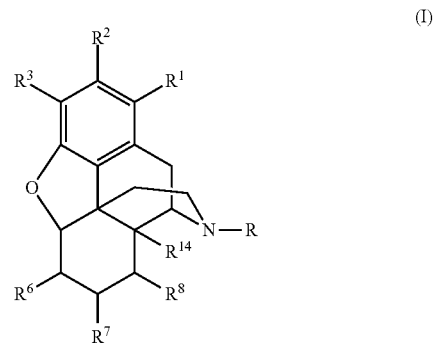

(I)

For each of the compounds comprising Formulas (I) or (II), the variables stand for the following:

R is selected from the group consisting of hydrogen, hydrocarbyl, and substituted hydrocarbyl, $R^1$ and $R^2$ are independently selected from the group consisting of hydrogen, hydrocarbyl, substituted hydrocarbyl, halogen, $\{-\}OR^{15}$, and hydroxy protecting group;

$R^3$, $R^7$, and $R^8$ are independently selected from the group consisting of hydrogen, hydrocarbyl, substituted hydrocarbyl, and $\{-\}OR^{15}$;

$R^6$ is selected from the group consisting of hydrogen, hydrocarbyl, substituted hydrocarbyl, $\{=\}O$, carbonyl protecting group, $\{-\}OR^{15}$, hydroxy protecting group, and $\{-\}NR^{16}R^{17}$;

$R^{14}$ is selected from the group consisting of hydrogen and $\{-\}OR^{16}$;

$R^{15}$ is selected from the group consisting of hydrocarbyl and substituted hydrocarbyl; and $R^{16}$ and $R^{17}$ are independently selected from the group consisting of hydrogen, hydrocarbyl, and substituted hydrocarbyl.

Other aspects and features of the invention are described in more detail below.

DETAILED DESCRIPTION

The present invention provides improved processes for the synthesis of 10-keto and/or 10-hydroxy morphinans, salts, intermediates, or analogs thereof. In particular, the processes of the invention comprise contacting a morphinan with an oxidizing system comprising a periodic acid and a chromium catalyst, wherein the morphinan undergoes benzylic oxidation to form the 10-keto morphinan. Moreover, the 10-keto morphinan may be reduced to form a 10-hydroxy morphinan. The processes of the invention, therefore, provide for the efficient synthesis of 10-keto and/or 10-hydroxy morphinans in good yields under mild reaction conditions.

(I) Processes for the Preparation of 10-Keto Morphinans and 10-Hydroxy Morphinans One aspect of the present invention provides processes for the synthesis of 10-keto morphinans. In general, the process comprises a benzylic oxidation of a morphinan comprising hydrogen substituents on C-10, wherein the 10-keto morphinan is formed. Specifically, the morphinan substrate is contacted with an oxidation system comprising a periodic acid and a chromium catalyst under mild reaction conditions, such that the 10-keto morphinan is synthesized.

In general, the morphinans detailed herein comprise any compound having a morphinan structure. For the purposes of illustration, the ring atoms of the core morphinan structure are

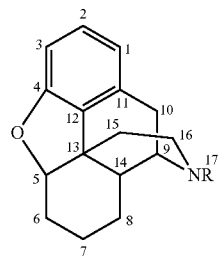

numbered as diagrammed above:
wherein R is selected from the group consisting of hydrogen, hydrocarbyl, and substituted hydrocarbyl.

Preferred R groups include hydrogen, alkyl, substituted alkyl, alkenyl, substituted alkenyl, aryl, and heterocyclo. Even more preferred R groups include hydrogen, methyl, ethyl, propyl, cyclopropyl, cyclopropylmethyl, butyl, isobutyl, t-butyl, cyclobutyl, cyclobutylmethyl, pentyl, isopenyl, neopentyl, cyclopentyl, and allyl.

Non-limiting examples of morphinans suitable for use as substrates in the process of this invention include aryl hydroxy protected buprenorphine derivatives, aryl hydroxy protected butorphanol derivatives, 6-hydroxy protected codeine derivatives, dextromethorphan, aryl hydroxy protected dextrorphan derivatives, 6-hydroxy protected dihydrocodeine derivatives, both aryl hydroxy and 6-hydroxy protected dihydromorphine derivatives, aryl hydroxy protected dihydrosinomenine derivatives, aryl hydroxy protected etorphine derivatives, 6-hydroxy protected ethylmorphine derivatives, hydrocodone, aryl hydroxy protected hydromorphone derivatives, levomethorphan, aryl hydroxy protected levorphanol derivatives, both aryl hydroxy and 6-hydroxy protected morphine derivatives, aryl hydroxy protected morphinone derivatives, both aryl hydroxy and 6-hydroxy protected nalbuphine derivatives, aryl hydroxy protected nalfurafine derivatives, aryl hydroxy protected naloxone derivatives, aryl hydroxy protected naltrexone derivatives, aryl hydroxy protected norbuprenorphine derivatives, 6-hydroxy protected norcodeine derivatives, nordextromethorphan, aryl hydroxy protected nordextrorphan derivatives, 6-hydroxy protected nordihydrocodeine derivatives, norhydrocodone, both aryl hydroxy and 6-hydroxy protected nordihydromorphine derivatives, aryl hydroxy protected norhydromorphone derivatives, aryl hydroxy protected nordihydrosinomenine derivatives, norlevomethorphan, aryl hydroxy protected norlevorphanol derivatives, both aryl hydroxy and 6-hydroxy protected normorphine derivatives, aryl hydroxy protected nororipavine derivatives, 6-hydroxy protected noroxycodol derivatives, noroxycodone, both aryl hydroxy and 6-hydroxy protected noroxymorphol derivatives, aryl hydroxy protected noroxymorphone derivatives, aryl hydroxy protected norsinomenine derivatives, northebaine, aryl hydroxy protected oripavine derivatives, oxycodeinone, oxycodone, aryl hydroxy protected oxymorphone derivatives, aryl hydroxy protected sinomenine derivatives, and thebaine.

In a further aspect of the invention, the 10-keto morphinan may be reduced to form a 10-hydroxy morphinan. Specifically, the 10-keto morphinan is contacted with a reducing agent to prepare the 10-hydroxy morphinan.

(II) Processes for the Preparation of Compounds Comprising Formula (II)

In preferred embodiments of the invention, a 10-keto morphinan comprising Formula (II) is synthesized from a morphinan comprising Formula (I). The process of the invention comprises contacting the compound comprising Formula (I) with an oxidizing system comprising a periodic acid and a chromium catalyst, wherein the compound comprising Formula (I) undergoes benzylic oxidation to form the 10-keto compound comprising Formula (II). For purposes of illustration, Reaction Scheme 1

Reaction Scheme 1:

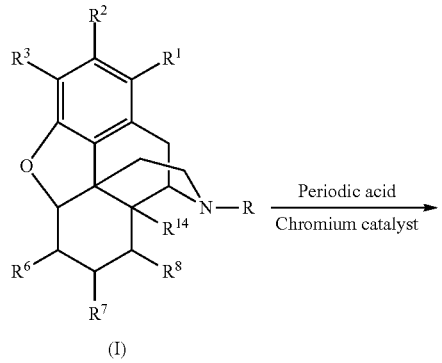

(I)

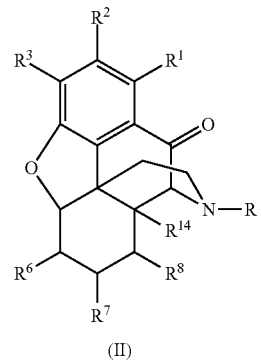

(II)

depicts the synthesis of the compound comprising Formula (II) in accordance with one aspect of the invention:
wherein:
R is selected from the group consisting of hydrogen, hydrocarbyl, and substituted hydrocarbyl;
$R^1$ and $R^2$ are independently selected from the group consisting of hydrogen, hydrocarbyl, substituted hydrocarbyl, halogen, {—}$OR^{15}$, and hydroxy protecting group;
$R^3$, $R^7$, and $R^8$ are independently selected from the group consisting of hydrogen, hydrocarbyl, substituted hydrocarbyl, and {—}$OR^{15}$;
$R^6$ is selected from the group consisting of hydrogen, hydrocarbyl, substituted hydrocarbyl, {=}O, carbonyl protecting group, {—}$OR^{15}$, hydroxy protecting group, and {—}$NR^{16}R^{17}$;
$R^{14}$ is selected from the group consisting of hydrogen and {—}$OR^{16}$;
$R^{15}$ is selected from the group consisting of hydrocarbyl and substituted hydrocarbyl; and
$R^{16}$ and $R^{17}$ are independently selected from the group consisting of hydrogen, hydrocarbyl, and substituted hydrocarbyl.

In a preferred iteration, $R^1$, $R^2$, $R^7$, and $R^8$ are hydrogen. In another preferred iteration, $R^{14}$ is hydrogen or hydroxy. In yet another preferred iteration, R is selected from the group consisting of hydrogen, alkyl, cycloalkyl, cycloalkylmethyl, alkenyl, aryl, and heterocycle. Preferably, R is selected from the group consisting of hydrogen, methyl, alkyl, cyclopropylmethyl, cyclobutylmethyl, and allyl. In still another preferred iteration, $R^3$ is selected from the group consisting of alkoxy, methoxy, and protected hydroxy. In another preferred iteration, $R^6$ is selected from the group consisting of hydrogen, protected hydroxy, alkoxy, keto, protected keto, ketal, amino, and amido.

(a) Reaction Mixture

The process of the invention commences with formation of a reaction mixture by combining the compound comprising Formula (I) with an oxidizing system comprising a periodic acid and a chromium catalyst. As detailed above, a variety of compounds comprising Formula (I) are suitable for use as a substrate in the process of the invention. In exemplary embodiments, for the compound comprising Formula (I), $R^1$, $R^2$, $R^7$, and $R^8$ are each hydrogen; R is hydrogen, methyl, cyclopropylmethyl, cyclobutylmethyl, or allyl; $R^3$ is alkoxy, methoxy, or protected hydroxy; $R^6$ is hydrogen, protected hydroxy, alkoxy, keto, protected keto, ketal, amino, or amido; and $R^{14}$ is hydrogen or hydroxy.

A variety of periodic acids may be used as oxidants in the process of the invention. Non-limiting examples of suitable periodic acids include orthoperiodic acid ($H_5IO_6$), metaperiodic acid ($HIO_4$), di-mesoperiodic acid ($H_4I_2O_9$), mesoperiodic acid ($H_3IO_5$), and di-orthoperiodic acid ($H_8I_2O_{11}$). In preferred embodiments, the periodic acid may be orthoperiodic acid ($H_5IO_6$).

Numerous chromium compounds may be used to catalyze the benzylic oxidation reaction. Suitable chromium catalysts include, without limit, chromium(II) oxide (CrO), chromium(III) oxide ($Cr_2O_3$), chromium(IV) oxide ($CrO_2$), chromium(VI) oxide or chromium trioxide ($CrO_3$), chromium trioxide/3,5-dimethylpyrazole complex, pyridinium chlorochromate (PCC), pyridinium dichromate (PDC), pyridinium fluorochromate (PFC), oxidodiperoxideochromium ($CrO_5$), a dichromate salt (e.g., $Na_2Cr_2O_7$, $K_2Cr_2O_7$, etc.), a chromate salt (e.g., $Na_2CrO_4$, $K_2CrO_4$, etc.), a chromium(III) halide (e.g., $CrCl_3$, $CrBr_3$, $CrF_3$, $CrI_3$, etc.), chromium nitrite ($Cr(NO_2)_3$), chromium acetate ($Cr(OAc)_3$), chromoyl diacetate ($CrO_2(OAc)_2$), and chromium perchlorate ($Cr(ClO_4)_3$). In preferred embodiments, the chromium catalyst may be chromium trioxide ($CrO_3$). In exemplary embodiments, the periodic acid is $H_5IO_6$ and the chromium catalyst is $CrO_3$.

The molar ratio of the compound comprising Formula (I) to the periodic acid can and will vary. In general, the molar ratio of the compound comprising Formula (I) to the periodic acid may range from about 1:1 to about 1:20. In various embodiments, the molar ratio of the compound comprising Formula (I) to the periodic acid may range from about 1:1 to about 1:3, from about 1:3 to about 1:10, or from about 1:10 to about 1:20. In preferred embodiments, the molar ratio of the compound comprising Formula (I) to the periodic acid may range from about 1:2 to about 1:10. In an exemplary embodiment, the molar ratio of the compound comprising Formula (I) to the periodic acid may be about 1:6.

The molar ratio of the compound comprising Formula (I) to the chromium catalyst may also vary. In general, the molar ratio of the compound comprising Formula (I) to the chromium catalyst may range from about 1:0.1 to about 1:20. In certain embodiments, the molar ratio of the compound comprising Formula (I) to the chromium catalyst may range from about 1:0.1 to about 1:1, from about 1:1 to about 1:5, or from about 1:5 to about 1:20. In preferred embodiments, the molar ratio of the compound comprising Formula (I) to the chromium catalyst may range from about 1:0.3 to about 1:1.5. In an exemplary embodiment, the molar ratio of the compound comprising Formula (I) to the chromium catalyst may be about 1:0.4.

The reaction mixture also comprises a solvent. The solvent can and will vary depending on the starting substrate and the oxidizing system used in the process. The solvent may be a protic solvent, an aprotic solvent, a non-polar solvent, or combinations thereof. Suitable examples of protic solvents include, but are not limited to, formic acid, acetic acid, water, t-butanol, and combinations thereof. Non-limiting examples of suitable aprotic solvents include acetone, acetonitrile, diethoxymethane, N,N-dimethylacetamide (DMAC), N,N-dimethylformamide (DMF), dimethyl sulfoxide (DMSO), N,N-dimethylpropionamide, 1,3-dimethyl-3,4,5,6-tetrahydro-2(1H)-pyrimidinone (DMPU), 1,3-dimethyl-2-imidazolidinone (DMI), 1,2-dimethoxyethane (DME), dimethoxymethane, bis(2-methoxyethyl)ether, 1,4-dioxane, N-methyl-2-pyrrolidinone (NMP), ethyl formate, ethyl methyl ketone, formamide, hexachloroacetone, hexamethylphosphoramide, N-methylacetamide, N-methylformamide, methylene chloride, nitrobenzene, nitromethane, propionitrile, sulfolane, tetramethylurea, tetrahydrofuran (THF), 2-methyl tetrahydrofuran, trichloromethane, and combinations thereof. Suitable examples of non-polar organic solvents include, but are not limited to, alkane and substituted alkane solvents (including cycloalkanes), aromatic hydrocarbons, esters, ethers, ketones, combinations thereof, and the like. Specific non-polar organic solvents that may be employed, include, for example, benzene, butyl acetate, t-butyl methylether, t-butyl methylketone, chlorobenzene, chloroform, chloromethane, cyclohexane, dichloromethane, dichloroethane, diethyl ether, ethyl acetate, diethylene glycol, fluorobenzene, heptane, hexane, isobutylmethylketone, isopropyl acetate, methyl acetate, methylethylketone, methyltetrahydrofuran, pentyl acetate, n-propyl acetate, tetrahydrofuran, toluene, and combinations thereof. In preferred embodiment, the solvent may be a mixture of acetonitrile and water, acetonitrile, t-butanol, dichloromethane, chloroform, chlorobenzene, ethyl acetate, acetone, methyl t-butyl ether, tetrahydrofuran, 2-methyltetrahydrofuran, N,N-dimethylformamide, or acetic acid. In one exemplary embodiment, the solvent may be acetonitrile. In another exemplary embodiment, the solvent may be a mixture of acetonitrile and water. Typically, the volume ratio of acetonitrile to water may range from about 0.3:1 to about 100:1. Preferably, the volume ratio of acetonitrile to water may be about 1:1.

In general, the weight ratio of the solvent to the compound comprising Formula (I) will range from about 1:1 to about 100:1. In various embodiments, the weight ratio of the solvent to the compound comprising Formula (I) may range from 1:1 to about 5:1, from about 5:1 to about 25:1, or from about 25:1 to about 100:1. In preferred embodiments, the weight ratio of the solvent to the compound comprising Formula (I) may range from about 20:1 to about 40:1. In an exemplary embodiment, the weight ratio of the solvent to the compound comprising Formula (I) may range from about 30:1 to about 35:1.

(b) Reaction Conditions

In general, the reaction may be conducted at a temperature that ranges from about −20° C. to about 120° C. In preferred embodiments, the reaction may be conducted at a temperature that ranges from about 10° C. to about 40° C. In various embodiments, the temperature of the reaction may be about 10° C., about 15° C., about 20° C., about room temperature (~23° C.), about 30° C., about 35° C., or about 40° C. In an exemplary embodiment, the reaction may be conducted at room temperature. Typically, the reaction is performed under ambient atmosphere and pressure.

Generally, the reaction is allowed to proceed for a sufficient period of time until the reaction is complete, as determined by any method known to one skilled in the art, such as chromatography (e.g., HPLC). In this context, a "completed reaction" generally means that the reaction mixture contains a significantly diminished amount of the compound comprising Formula (I). Typically, the amount of the compound comprising Formula (I) remaining in the reaction mixture at the end of the reaction may be less than about 3%, and preferably less than about 1%. The duration of the reaction may range from about 1 hour to about 48 hours. In various embodiments, the reaction may be allowed to proceed for 1, 2, 3, 4, 5, 6, 8, 10, 12, 14, 16, 18, 20, 24, 30, 36, 42, or 48 hours.

The compound comprising Formula (II) may be isolated form the reaction mixture using techniques known to those of skill in the art. Non-limiting examples of suitable techniques include extraction, precipitation, concentration, chromatography, and crystallization.

The yield of the compound comprising Formula (II) can and will vary. Typically, the yield of the compound comprising Formula (II) may be at least about 40%. In one embodiment, the yield of the compound comprising Formula (II) may range from about 40% to about 60%. In another embodiment, the yield of the compound comprising Formula (II) may range from about 60% to about 80%. In a further embodiment, the yield of the compound comprising Formula (II) may range from about 80% to about 90%. In still another embodiment, the yield of the compound comprising Formula (II) may be greater than about 90%.

The compound comprising Formula (II) may be used as is or it may be converted to another compound using techniques familiar to those of skill in the art. As an example, for compounds comprising Formula (II) in which $R^1$, $R^2$, $R^3$, $R^7$, $R^8$, and/or $R^{14}$ comprise a methoxy group, the compound may undergo a demethylation reaction to form a compound comprising a hydroxyl group at that position(s). As another example, for compounds comprising Formula (II) in which R is hydrocarbyl or substituted hydrocarbyl, the compound may be converted into a normorphinan, i.e., R is hydrogen.

(III) Processes for the Preparation of Compounds Comprising Formula (III)

In a further aspect of the invention, the compound comprising Formula (II) may be contacted with a reducing agent to form a compound comprising Formula (III). For the purposes of illustration, Reaction Scheme 2 depicts the synthesis of the compound comprising Formula (III) in accordance with this aspect of the invention:

Reaction Scheme 2:

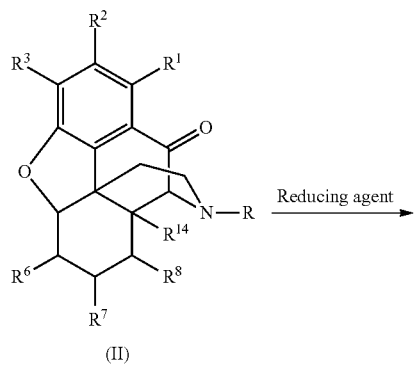

(II)

→ Reducing agent

-continued

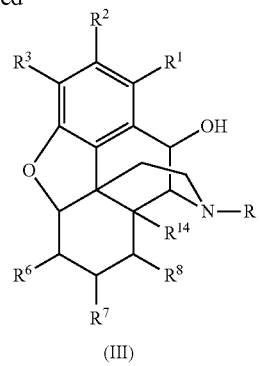

(III)

wherein R, $R^1$, $R^2$, $R^3$, $R^6$, $R^7$, $R^8$, and $R^{14}$ are as defined above in Reaction Scheme 1.

A variety of reducing agents are suitable for use in reducing the 10-keto moiety to a 10-hydroxy moiety. Non-limiting example of suitable reducing agents include hydrides (e.g., hydrogen iodide, hydrogen sulfide, lithium aluminum hydride, sodium borohydride, sodium cyanoborohydride, and the like), or combinations of a metal (e.g., tin, zinc, or iron) or a metal compound (e.g., chromium chloride, chromium acetate, and the like) with an organic or inorganic acid (e.g., formic acid, acetic acid, propionic acid, trifluoroacetic acid, p-toluenesulfonic acid, hydrochloric acid, and the like), samarium iodide, and others. In preferred embodiments, the reducing agent may be aluminum hydride, borane-tetrahydrofuran, catecholborane, diisobutylaluminum hydride, disiamylborane, lithium aluminum hydride, lithium borohydride, lithium tri-t-butoxyaluminum hydride, lithium triethylborohydride, potassium tri-s-butylborohydride, sodium borohydride, sodium cyanoborohydride, or sodium triacetoxyborohydride. In exemplary embodiments, the reducing agent may be sodium borohydride or lithium borohydride.

The molar ratio of the compound comprising Formula (II) to the reducing agent can and will vary. In general, the molar ratio of the compound comprising Formula (II) to the reducing agent may range from about 1:1 to about 1:10. In preferred embodiments, the molar ratio of the compound comprising Formula (II) to the reducing agent may range from about 1:2 to about 1:5. In various preferred embodiments, the molar ratio of the compound comprising Formula (II) to the reducing agent may be about 1:2, about 1:3, about 1:4, or about 1:5.

Contact between the compound comprising Formula (II) and the reducing agent typically occurs in the presence of a solvent. Examples of suitable solvents are detailed above in section (II)(a). In preferred embodiments, the solvent may be methanol, tetrahydrofuran, ether, or toluene. In exemplary embodiments, the solvent may be methanol or tetrahydrofuran. In general, the weight ratio of the solvent to the compound comprising Formula (II) may range from about 1:1 to about 100:1.

In general, the reaction may be conducted at a temperature that ranges from about −80° C. to about 110° C. In preferred embodiments, the reaction may be conducted at a temperature that ranges from about 0"C to about 40° C. Typically, the reaction is performed under ambient atmosphere and pressure.

Generally, the reaction is allowed to proceed for a sufficient period of time until the reaction is complete, as determined by any method known to one skilled in the art, such as chromatography (e.g., HPLC). In this context, a "completed reaction" generally means that the reaction mixture contains a significantly diminished amount of the compound comprising Formula (II). Typically, the amount of the compound comprising Formula (II) remaining in the reaction mixture at the end of the reaction may be less than about 3%, and preferably less than about 1%.

The compound comprising Formula (III) may be isolated form the reaction mixture using techniques known to those of skill in the art. Non-limiting examples of suitable techniques include extraction, precipitation, concentration, chromatography, and crystallization. The compound comprising Formula (III) may be used as is or it may be converted to another compound using techniques familiar to those of skill in the art.

The yield of the compound comprising Formula (III) can and will vary. Typically, the yield of the compound comprising Formula (III) may be at least about 60%. In one embodiment, the yield of the compound comprising Formula (III) may range from about 60% to about 70%. In another embodiment, the yield of the compound comprising Formula (III) may range from about 70% to about 80%. In a further embodiment, the yield of the compound comprising Formula (III) may range from about 80% to about 90%. In still another embodiment, the yield of the compound comprising Formula (III) may be greater than about 90%.

Additionally, each of compounds comprising Formulas (II) or (III) may be converted to a pharmaceutically acceptable salt. Pharmaceutically acceptable salts include, without limitation, acetate, aspartate, benzoate, bitartrate, citrate, formate, gluconate, glucuronate, glutamate, fumarate, hydrochloride, hydrobromide, hydroiodide, hypophosphite, isobutyrate, isocitrate, lactate, malate, maleate, meconate, methylbromide, methanesulfonate, monohydrate, mucate, nitrate, oxalate, phenylpropionate, phosphate, phthalate, propionate, pyruvate, salicylate, stearate, succinate, sulfate, tannate, tartrate, terephthalate, valerate, and the like.

The compounds comprising any of Formulas (I), (II), or (III) may have a (−) or a (+) orientation with respect to the rotation of polarized light. More specifically, each chiral center of the morphinan may have an R or an S configuration. The compounds described herein may have at least four chiral centers, namely carbons C-5, C-9, C-13, and C-14. At each chiral center, the stereochemistry at the carbon atom is independently R or S. The configuration of C-5, C-9, C-13, and C-14, respectively, may be RRRR, RRRS, RRSR, RSRR, SRRR, RRSS, RSSR, SSRR, SRRS, SRSR, RSRS, RSSS, SRSS, SSRS, SSSR, or SSSS, provided that the C-15 and C-16 atoms are both on the alpha face of the molecule or both on the beta face of the molecule. For compounds comprising Formula (III), the 10-hydroxy group may have an alpha or a beta configuration (and may be R or S). Moreover, the reaction product of the reduction of the compound comprising Formula (II) may be 10-alpha-hydroxy, 10-beta-hydroxy, or a mixture thereof.

Definitions

The compounds described herein have asymmetric centers. Compounds of the present invention containing an asymmetrically substituted atom may be isolated in optically active or racemic form. All chiral, diastereomeric, racemic forms and all geometric isomeric forms of a structure are intended, unless the specific stereochemistry or isomeric form is specifically indicated.

The term "acyl," as used herein alone or as part of another group, denotes the moiety formed by removal of the hydroxy group from the group COOH of an organic carboxylic acid, e.g., RC(O)—, wherein R is $R^1$, $R^1O$—, $R^1R^2N$—, or $R^1S$—, $R^1$ is hydrocarbyl, heterosubstituted hydrocarbyl, or heterocyclo, and $R^2$ is hydrogen, hydrocarbyl, or substituted hydrocarbyl.

The term "acyloxy," as used herein alone or as part of another group, denotes an acyl group as described above bonded through an oxygen linkage (O), e.g., RC(O)O— wherein R is as defined in connection with the term "acyl."

The term "allyl," as used herein not only refers to compound containing the simple allyl group ($CH_2$=CH—$CH_2$—), but also to compounds that contain substituted allyl groups or allyl groups forming part of a ring system.

The term "allyl-transition metal catalyst," as used herein refers to coordination compounds in which a transition metal ion is complexed with at least one allyl ligand (or substituted allyl ligand) via delocalized eta ($\eta^3$) bonds. The superscript refers to the number of electrons shared between the metal center and the allyl ligand.

The term "alkyl" as used herein describes groups which are preferably lower alkyl containing from one to eight carbon atoms in the principal chain and up to 20 carbon atoms. They may be straight or branched chain or cyclic and include methyl, ethyl, propyl, isopropyl, butyl, hexyl and the like.

The term "alkenyl" as used herein describes groups which are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

The term "alkynyl" as used herein describes groups which are preferably lower alkynyl containing from two to eight carbon atoms in the principal chain and up to 20 carbon atoms. They may be straight or branched chain and include ethynyl, propynyl, butynyl, isobutynyl, hexynyl, and the like.

As used herein, the term "6-amino" encompasses primary and secondary amine moieties conjugated to C-6 of a morphinan.

The term "aromatic" as used herein alone or as part of another group denotes optionally substituted homo- or heterocyclic conjugated planar ring or ring system comprising delocalized electrons. These aromatic groups are preferably monocyclic (e.g., furan or benzene), bicyclic, or tricyclic groups containing from 5 to 14 atoms in the ring portion. The term "aromatic" encompasses "aryl" groups defined below.

The terms "aryl" or "Ar" as used herein alone or as part of another group denote optionally substituted homocyclic aromatic groups, preferably monocyclic or bicyclic groups containing from 6 to 10 carbons in the ring portion, such as phenyl, biphenyl, naphthyl, substituted phenyl, substituted biphenyl, or substituted naphthyl.

The terms "carbocyclo" or "carbocyclic" as used herein alone or as part of another group denote optionally substituted, aromatic or non-aromatic, homocyclic ring or ring system in which all of the atoms in the ring are carbon, with preferably 5 or 6 carbon atoms in each ring. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro, and thio.

The terms "halogen" or "halo" as used herein alone or as part of another group refer to chlorine, bromine, fluorine, and iodine.

The term "heteroatom" refers to atoms other than carbon and hydrogen.

The term "heteroaromatic" as used herein alone or as part of another group denotes optionally substituted aromatic groups having at least one heteroatom in at least one ring, and preferably 5 or 6 atoms in each ring. The heteroaromatic group preferably has 1 or 2 oxygen atoms and/or 1 to 4 nitrogen atoms in the ring, and is bonded to the remainder of the molecule through a carbon. Exemplary groups include furyl, benzofuryl, oxazolyl, isoxazolyl, oxadiazolyl, benzoxazolyl, benzoxadiazolyl, pyrrolyl, pyrazolyl, imidazolyl, triazolyl, tetrazolyl, pyridyl, pyrimidyl, pyrazinyl, pyridazinyl, indolyl, isoindolyl, indolizinyl, benzimidazolyl, indazolyl, benzotriazolyl, tetrazolopyridazinyl, carbazolyl, purinyl, quinolinyl, isoquinolinyl, imidazopyridyl, and the like. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro, and thio.

The terms "heterocyclo" or "heterocyclic" as used herein alone or as part of another group denote optionally substituted, fully saturated or unsaturated, monocyclic or bicyclic, aromatic or non-aromatic groups having at least one heteroatom in at least one ring, and preferably 5 or 6 atoms in each ring. The heterocyclo group preferably has 1 or 2 oxygen atoms and/or 1 to 4 nitrogen atoms in the ring, and is bonded to the remainder of the molecule through a carbon or heteroatom. Exemplary heterocyclo groups include heteroaromatics as described above. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro, and thio.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The term "protecting group" as used herein denotes a group capable of protecting an oxygen atom or a nitrogen atom, wherein the protecting group may be removed, subsequent to the reaction for which protection is employed, without disturbing the remainder of the molecule. Exemplary hydroxy protecting groups include ethers (e.g., allyl, triphenylmethyl (trityl or Tr), p-methoxybenzyl (PMB), p-methoxyphenyl(PMP)), acetals (e.g., methoxymethyl (MOM), β-methoxyethoxymethyl (MEM), tetrahydropyranyl (THP), ethoxy ethyl (EE), methylthiomethyl (MTM), 2-methoxy-2-propyl (MOP), 2-trimethylsilylethoxymethyl (SEM)), esters (e.g., benzoate (Bz), allyl carbonate, 2,2,2-trichloroethyl carbonate (Troc), 2-trimethylsilylethyl carbonate), and silyl ethers (e.g., trimethylsilyl (TMS), triethylsilyl (TES), triisopropylsilyl (TIPS), triphenylsilyl (TPS), t-butyldimethylsilyl (TBDMS), t-butyldiphenylsilyl (TBDPS) and the like). Exemplary nitrogen protecting groups include tertiary amines (e.g., benzyl, p-methoxybenzyl, allyl, trityl), amides (e.g., acdtyl, trichloroacetamide, trifluoroacetamide, pent-4-enamide), imides (e.g., phthalimide, chlorinated phthalimides), carbamates (e.g., tert-butyloxycarbonyl (Boc), carbobenzyloxy (Cbz), allyoxycarbonyl (alloc), 9H-fluoren-9-ylmethoxycarbonyl (Fmoc), N-trichloroethoxycarbonyl (Troc), sulfonamides (e.g., tosyl), and the like. A variety of protecting groups and the synthesis thereof may be found in "Protective Groups in Organic Synthesis" by T. W. Greene and P. G. M. Wuts, John Wiley & Sons, Fourth Edition, 2007.

The "substituted hydrocarbyl" moieties described herein are hydrocarbyl moieties which are substituted with at least one atom other than carbon, including moieties in which a carbon chain atom is substituted with a heteroatom such as nitrogen, oxygen, silicon, phosphorous, boron, or a halogen atom, and moieties in which the carbon chain comprises additional substituents. These substituents include alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro, and thio.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

Having described the invention in detail, it will be apparent that modifications and variations are possible without departing from the scope of the invention defined in the appended claims.

EXAMPLES

The following examples are included to demonstrate preferred embodiments of the invention. It should be appreciated by those of skill in the art that the techniques disclosed in the examples represent techniques discovered by the inventors to function well in the practice of the invention. Those of skill in the art should, however, in light of the present disclosure, appreciate that many changes can be made in the specific embodiments that are disclosed and still obtain a like or similar result without departing from the spirit and scope of the invention, therefore all matter set forth is to be interpreted as illustrative and not in a limiting sense.

Example 1

Synthesis of 10-Keto Hydrocodone

The following reaction scheme depicts the preparation of 10-keto hydrocodone:

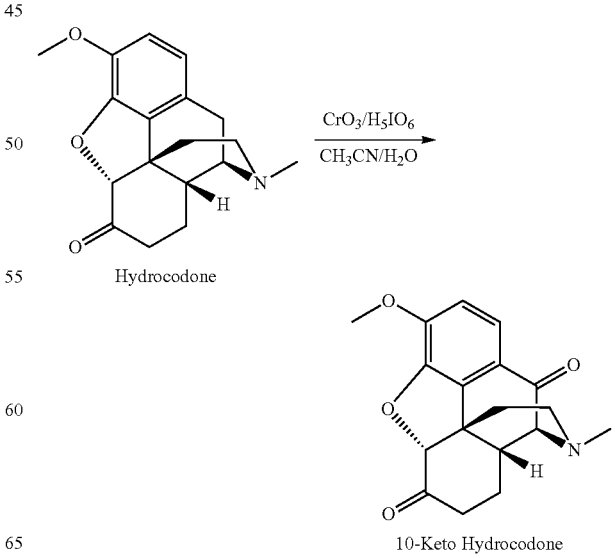

H$_5$IO$_6$ (19.147 g, 84 mmol) was dissolved in H$_2$O (70 mL). Hydrocodone (4.191 g, 14 mmol) was added to this solution and was dissolved by adding CH$_3$CN (70 mL). CrO$_3$ (560 mg, 5.6 mmol) was added to the mixture. The reaction mixture was stirred at room temperature for 4 h to complete the reaction. The reaction was neutralized with saturated NaHCO$_3$, and extracted with chloroform. After workup, concentration, and column chromatographic purification (0 to 5% MeOH in CHCl$_3$), 2.66 g of 10-keto hydrocodone (8.49 mmol, 61% yield) was obtained.

Example 2

Synthesis of 10-Keto Oxycodone

The following reaction scheme depicts the preparation of 10-keto Oxycodone:

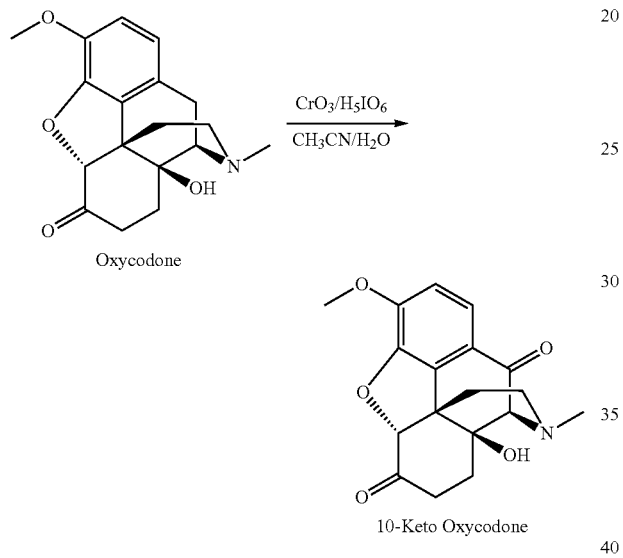

H$_5$IO$_6$ (1.368 g, 6 mmol) was dissolved in H$_2$O (5 mL). Oxycodone (315 mg, 1 mmol) was added to this solution and was dissolved by adding CH$_3$CN (5 mL). CrO$_3$ (40 mg, 0.4 mmol) was added to the mixture. The reaction mixture was stirred at room temperature for 4 h to complete the reaction. The reaction was neutralized with saturated NaHCO$_3$, and extracted with chloroform. After workup, concentration, and column chromatographic purification (0 to 5% MeOH in CHCl$_3$), 210 mg of 10-keto oxycodone (0.64 mmol, 64% yield) was obtained.

What is claimed is:

1. A process for preparing a 10-keto morphinan, the process comprising contacting a pentacyclic morphinan comprising hydrogen substituents on C-10 with an oxidizing system comprising a periodic acid and a chromium catalyst to form the 10-keto morphinan, wherein the yield of the 10-keto morphinan is at least about 40%.

2. The process of claim 1, wherein the periodic acid is chosen from H$_5$IO$_6$, HIO$_4$, H$_4$I$_2$O$_9$, H$_3$IO$_5$, and H$_8$I$_2$O$_{11}$.

3. The process of claim 1, wherein chromium catalyst is chosen from CrO, Cr$_2$O$_3$, CrO$_2$, CrO$_3$, CrO$_3$/3,5-dimethylpyrazole complex, pyridinium chlorochromate, pyridinium dichromate, pyridinium fluorochromate, CrO$_5$, Na$_2$CrO$_7$, K$_2$CrO$_7$, Na$_2$CrO$_4$, K$_2$CrO$_4$, CrCl$_3$, CrBr$_3$, CrF$_3$, CrI$_3$, Cr(NO$_2$)$_3$, Cr(OAc)$_3$, CrO$_2$(OAc)$_2$, and Cr(ClO$_4$)$_3$.

4. The process of claim 1, wherein the periodic acid is H$_5$IO$_6$ and the chromium catalyst is CrO$_3$.

5. The process of claim 1, wherein the 10-keto morphinan is contacted with a reducing agent to form a 10-hydroxy morphinan.

6. A process for preparing a compound of Formula (II):

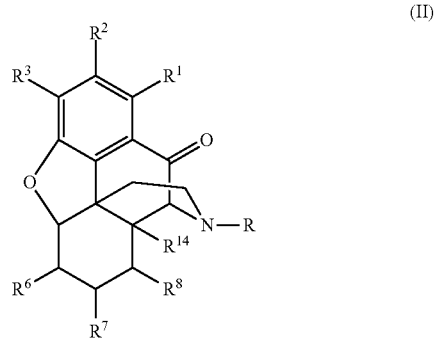

the process comprising:
contacting a compound of Formula (I):

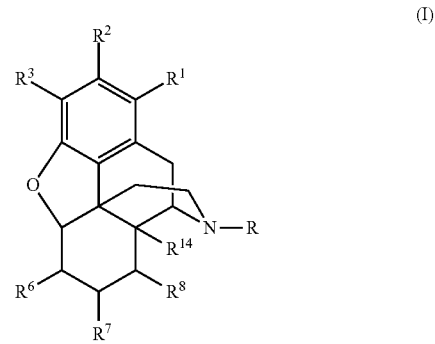

with an oxidizing system comprising a periodic acid and a chromium catalyst to form the compound of Formula (II), wherein:
R is chosen from hydrogen, hydrocarbyl, and substituted hydrocarbyl;
R$^1$ and R$^2$ are independently chosen from hydrogen, hydrocarbyl, substituted hydrocarbyl, halogen, {—}OR$^{15}$, and hydroxy protecting group;
R$^3$, R$^7$, and R$^8$ are independently chosen from hydrogen, hydrocarbyl, substituted hydrocarbyl, and {—}OR$^{15}$;
R$^6$ is chosen from hydrogen, hydrocarbyl, substituted hydrocarbyl, {═}O, carbonyl protecting group, {—}OR$^{15}$, hydroxy protecting group, and {—}NR$^{16}$R$^{17}$;
R$^{14}$ is chosen from hydrogen and {—}OR$^{16}$;
R$^{15}$ is chosen from hydrocarbyl and substituted hydrocarbyl; and
R$^{16}$ and R$^{17}$ are independently chosen from hydrogen, hydrocarbyl, and substituted hydrocarbyl,
and further wherein the yield of the compound of Formula (II) is at least about 40%.

7. The process of claim 6, wherein R$^1$, R$^2$, R$^7$, and R$^8$ are hydrogen; R$^{14}$ is hydrogen or hydroxy; R is chosen from hydrogen, alkyl, cycloalkyl, cycloalkylmethyl, alkenyl, aryl, and heterocyclo; R$^3$ is chosen from alkoxy, methoxy, and protected hydroxy; and $R^6$ is chosen from hydrogen, protected hydroxy, alkoxy, keto, protected keto, ketal, and amido.

8. The process of claim 6, wherein the periodic acid is chosen from $H_5IO_6$, $HIO_4$, $H_4I_2O_9$, $H_3IO_5$, and $H_8I_2O_{11}$; the chromium catalyst is chosen from CrO, $Cr_2O_3$, $CrO_2$, $CrO_3$, $CrO_3$/3,5-dimethylpyrazole complex, pyridinium chlorochromate, pyridinium dichromate, pyridinium fluorochromate, $CrO_5$, $Na_2CrO_7$, $K_2CrO_7$, $Na_2CrO_4$, $K_2CrO_4$, $CrCl_3$, $CrBr_3$, $CrF_3$, $CrI_3$, $Cr(NO_2)_3$, $Cr(OAc)_3$, $CrO_2(OAc)_2$, and $Cr(ClO_4)_3$; the molar ratio of the compound of Formula (I) to the periodic acid to the chromium catalyst is from about 1:1:0.1 to about 1:20:20; and the reaction is conducted at a temperature from about −20° to about 120° C.

9. The process of claim 6, wherein the periodic acid is $H_5IO_6$ and the chromium catalyst is $CrO_3$.

10. The process of claim 6, wherein the reaction is conducted in the presence of a solvent chosen from acetonitrile, a mixture of acetonitrile and water, t-butanol, dichloromethane, chloroform, chlorobenzene, ethyl acetate, acetone, methyl t-butyl ether, tetrahydrofuran, 2-methyltetrahydrofuran, N,N-dimethylformamide, and acetic acid; and the weight ratio of the solvent to the compound of Formula (II) is from about 1:1 to about 100:1.

11. The process of claim 6, wherein the periodic acid is $H_5IO_6$ and the chromium catalyst is $CrO_3$; the molar ratio of the compound of Formula (I) to $H_5IO_6$ to $CrO_3$ is from about 1:1:0.1 to about 1:10:1.5; the reaction is conducted in the presence of a solvent comprising acetonitrile and water; the weight ratio of the solvent to the compound of Formula (I) is about 20:1 to about 40:1; the reaction is conducted at temperature from about 10° to about 40° C.; and the yield of the compound of Formula (II) is at least about 40%.

12. The process of claim 6, wherein the compound of Formula (II) is contacted with a reducing agent to form a compound of Formula (III):

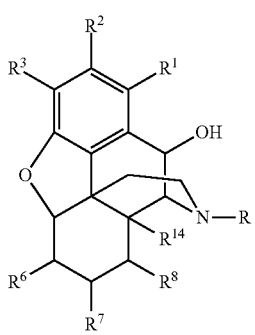

(III)

wherein:
R is chosen from hydrogen, hydrocarbyl, and substituted hydrocarbyl;

$R^1$ and $R^2$ are independently chosen from hydrogen, hydrocarbyl, substituted hydrocarbyl, halogen, {—}$OR^{15}$, and hydroxy protecting group;

$R^3$, $R^7$, and $R^8$ are independently chosen from hydrogen, hydrocarbyl, substituted hydrocarbyl, and {—}$OR^{15}$;

$R^6$ is chosen from hydrogen, hydrocarbyl, substituted hydrocarbyl, {=}O, carbonyl protecting group, {—}$OR^{15}$, hydroxy protecting group, and {—}$NR^{16}R^{17}$;

$R^{14}$ is chosen from hydrogen and {—}$OR^{16}$;

$R^{15}$ is chosen from hydrocarbyl and substituted hydrocarbyl; and $R^{16}$ and $R^{17}$ are independently chosen from hydrogen, hydrocarbyl, and substituted hydrocarbyl.

13. The process of claim 12, wherein $R^1$, $R^2$, $R^7$, and $R^8$ are hydrogen; $R^{14}$ is hydrogen or hydroxyl; R is chosen from hydrogen, alkyl, cycloalkyl, cycloalkylmethyl, alkenyl, aryl, and heterocyclo; $R^3$ is chosen from alkoxy, methoxy, and protected hydroxy; and $R^6$ is chosen from hydrogen, protected hydroxy, alkoxy, keto, protected keto, ketal, amino, and amido.

14. The process of claim 12, wherein the reducing agent is chosen from aluminum hydride, borane-tetrahydrofuran, catecholborane, diisobutylaluminum hydride, disiamylborane, lithium aluminum hydride, lithium borohydride, lithium tri-t-butoxyaluminum hydride, lithium triethylborohydride, potassium tri-s-butylborohydride, sodium borohydride, sodium cyanoborohydride, and sodium triacetoxyborohydride; and the molar ratio of the compound of Formula (II) to the reducing agent is from about 1:1 to about 1:10.

15. The process of claim 12, wherein the reaction is conducted in the present of a solvent chosen from methanol, tetrahydrofuran, ether, and toluene.

16. The process of claim 12, wherein the reaction is conducted at a temperature from about −80° C. to about 110° C.

17. The process of claim 12, wherein the reducing agent is chosen from sodium borohydride and lithium borohydride; the molar ratio of the compound of Formula (II) to the reducing agent is from about 1:2 to about 1:5; the reaction is conducted in the presence of a solvent chosen from methanol and tetrahydrofuran and at a temperature from about 0° to about 40° C.; and the yield of the compound of Formula (III) is at least about 60%.

18. The process of claim 12, wherein the optical activity of the compounds of Formulas (I), (II), or (III) is (−) or (+), and the configuration of C-5, C-13, C-14, and C-9, respectively, is chosen from RRRR, RRRS, RRSR, RSRR, SRRR, RRSS, RSSR, SSRR, SRRS, SRSR, RSRS, RSSS, SRSS, SSRS, SSSR, and SSSS, provided that C-15 and C-16 are both either on the alpha face or the beta face of the molecule.

19. The process of claim 12, wherein the reaction product comprises 10-alpha-hydroxy epimers, 10-beta-hydroxy epimers, or a combination thereof.

* * * * *